United States Patent
Drewry et al.

[19]

[11] Patent Number: 5,947,966
[45] Date of Patent: Sep. 7, 1999

[54] DEVICE FOR LINKING ADJACENT RODS IN SPINAL INSTRUMENTATION

[75] Inventors: Troy Drewry; Michael C. Sherman, both of Memphis; James E. Van Hoeck, Cordova, all of Tenn.; Denis S. Drummond, Narberth, Pa.; David L. Brumfield, Southhaven, Miss.; M. Neil Anderson, Memphis, Tenn.

[73] Assignee: SDGI Holdings, Inc., Wilminington, Del.

[21] Appl. No.: 08/946,954

[22] Filed: Oct. 8, 1997

Related U.S. Application Data

[63] Continuation of application No. 08/608,733, Feb. 29, 1996, abandoned, which is a continuation-in-part of application No. 08/469,222, Jun. 6, 1995, abandoned.

[51] Int. Cl.⁶ .................................................. A61B 17/58
[52] U.S. Cl. ................................................. 606/61; 606/72
[58] Field of Search ................................ 606/60, 61, 72, 606/73

[56] References Cited

U.S. PATENT DOCUMENTS

| | | |
|---|---|---|
| 2,638,301 | 5/1953 | Smith . |
| 3,499,222 | 3/1970 | Linkow et al. . |
| 4,641,636 | 2/1987 | Cotrel ........................................ 128/69 |
| 4,773,402 | 9/1988 | Asher et al. .............................. 128/69 |
| 4,957,495 | 9/1990 | Kluger ...................................... 606/58 |
| 5,002,542 | 3/1991 | Frigg ........................................ 606/61 |
| 5,005,562 | 4/1991 | Cotrel ...................................... 128/69 |
| 5,024,213 | 6/1991 | Asher et al. .............................. 128/69 |
| 5,030,220 | 7/1991 | Howland .................................. 606/61 |
| 5,102,412 | 4/1992 | Rogozinski .............................. 606/61 |

(List continued on next page.)

FOREIGN PATENT DOCUMENTS

| | | |
|---|---|---|
| 0 446 092 | 2/1991 | European Pat. Off. . |
| 2 645 427 | 4/1989 | France . |
| 2714590 | 7/1995 | France . |
| 3219575A1 | 12/1983 | Germany . |
| 43 30 837 A1 | 3/1995 | Germany . |
| 2 208 476 | 4/1989 | United Kingdom . |
| WO 90/04948 | 5/1990 | WIPO . |
| WO 95/13754 | 5/1995 | WIPO . |

OTHER PUBLICATIONS

*TSRH Crosslink Components*, Danek Medical, Inc. Copyright 1990.
*TSRH Crosslink*, Danek Medical, 1987.

Primary Examiner—Michael Buiz
Assistant Examiner—Daphna Shai
Attorney, Agent, or Firm—Woodard, Emhardt, Naughton, Moriarty & McNett

[57] ABSTRACT

One embodiment of a spinal fixation system including a pair of longitudinal members 11, 12 positionable adjacent the spine, means for engaging longitudinal members to the spine 13, 14, a pair of wedge members 241 each having a bearing surface 242 configured to bear on a longitudinal member 11, 12, and a connector 200 configured to span a distance between the longitudinal members 11, 12. The connector 200 includes a pair of engaging members 205, 212 each having a fixation portion 207, 214 and a connecting portion 209, 216, and a bridge members 202 attachable to the connecting portions 209, 216. The engaging members 205, 212 each define a thru-hole 225 for receiving one of the wedge members 241. The thru-holes 225 are aligned so that when one of the wedge members 241 is advanced through the thru-hole 225, the bearing surface 242 will bear on a corresponding longitudinal member 11, 12 to force the longitudinal member 11, 12 into contact with the fixation surface 220, 221 and engage the longitudinal member 11, 12 to the connector 200. In a specific embodiment, the bridge member 200 defines a slot 203 and a fastener bore 227 having an axis D' intersecting the slot 203. In this embodiment, the second connecting portion 216 is insertable into the slot 203 to intersect the axis D' of the bone 227, whereby a fastener 230 received in the bore 227 will clamp the second connecting portion 216 to the bridge member 202.

20 Claims, 17 Drawing Sheets

U.S. PATENT DOCUMENTS

| | | | |
|---|---|---|---|
| 5,129,900 | 7/1992 | Asher et al. | 606/61 |
| 5,133,716 | 7/1992 | Plaza | 606/61 |
| 5,147,359 | 9/1992 | Cozad et al. | 606/61 |
| 5,147,360 | 9/1992 | Dubousset | 606/61 |
| 5,154,718 | 10/1992 | Cozad et al. | 606/61 |
| 5,275,600 | 1/1994 | Allard et al. . | |
| 5,312,405 | 5/1994 | Korotko et al. | 606/61 |
| 5,330,473 | 7/1994 | Howland | 606/61 |
| 5,334,203 | 8/1994 | Wagner | 606/61 |
| 5,368,594 | 11/1994 | Martin et al. | 606/61 |
| 5,403,316 | 4/1995 | Ashman | 606/61 |
| 5,439,463 | 8/1995 | Lin | 606/61 |
| 5,522,816 | 6/1996 | Dinello et al. | 606/61 |
| 5,601,552 | 2/1997 | Cotrel . | |
| 5,630,816 | 5/1997 | Kambin . | |

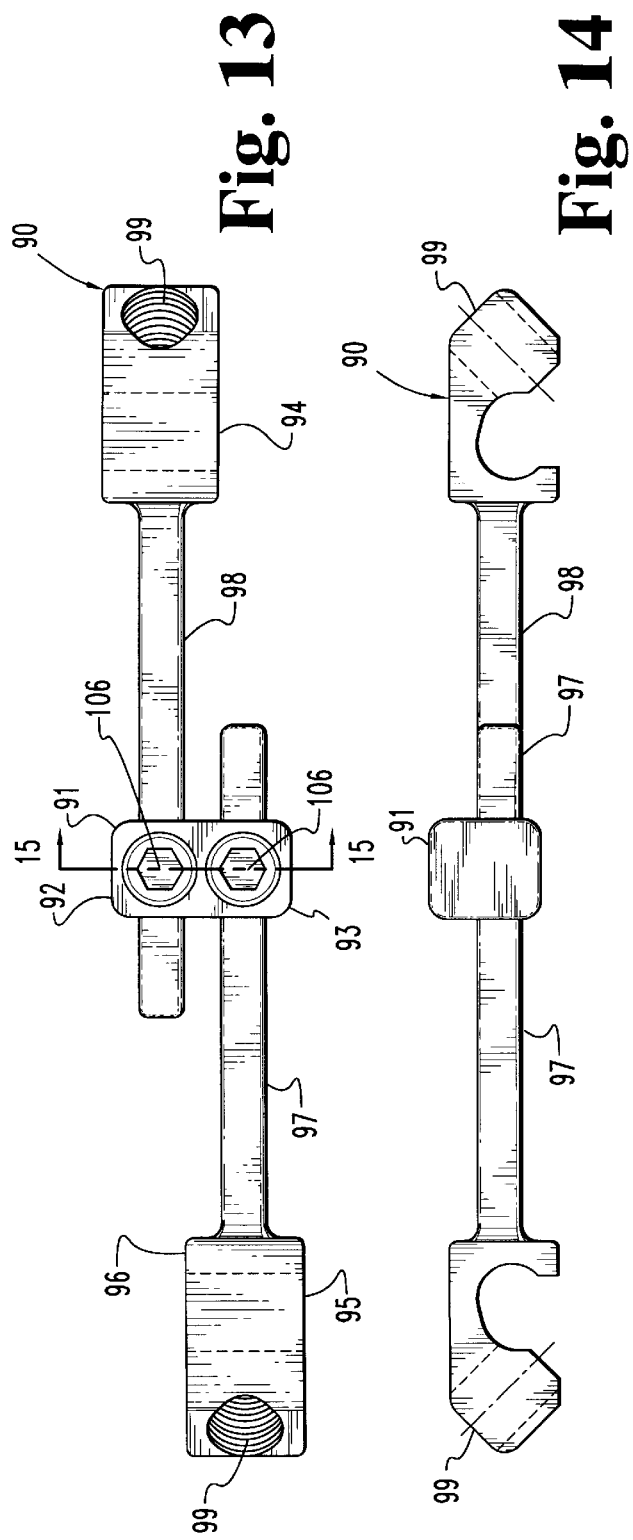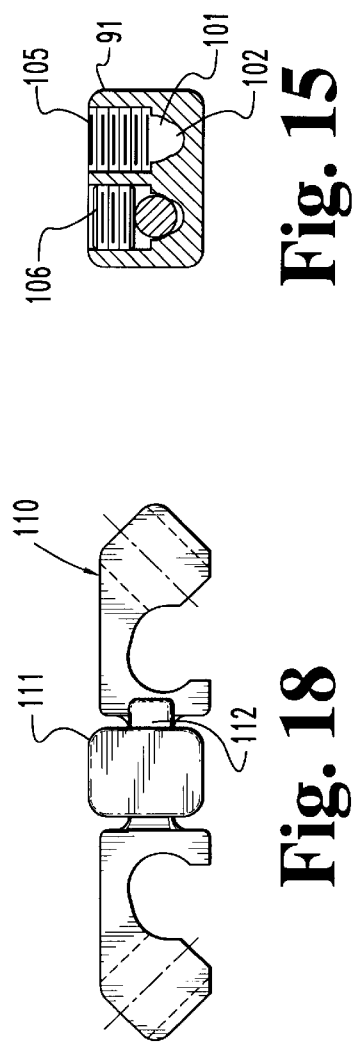

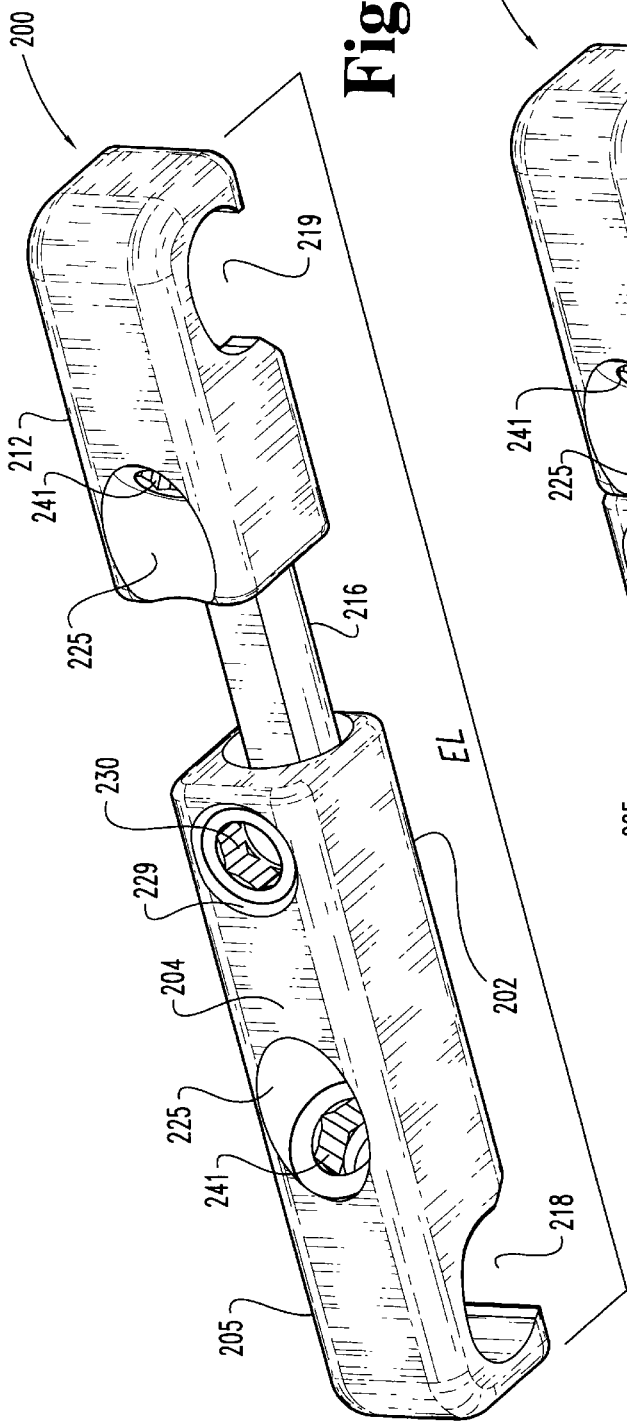
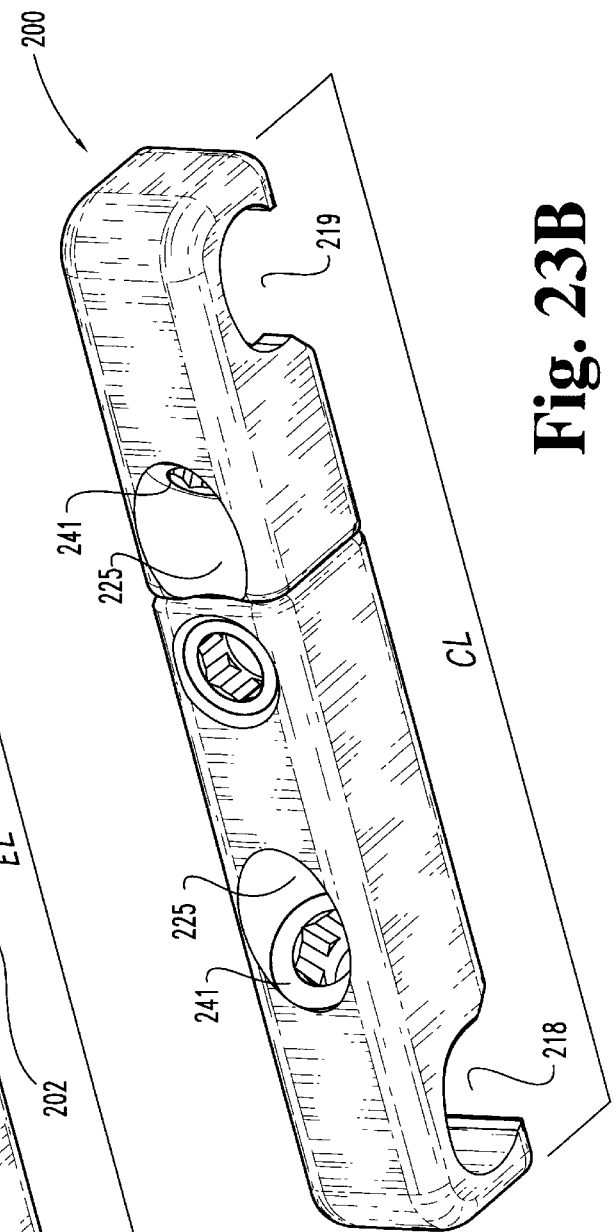
Fig. 23A
Fig. 23B

DEVICE FOR LINKING ADJACENT RODS IN SPINAL INSTRUMENTATION

REFERENCE TO RELATED APPLICATIONS

This application is a continuation of application Ser. No. 08/608,733, filed Feb. 29, 1996, now abandoned, which is a continuation-in-part of application Ser. No. 08/469,222, filed Jun. 6, 1995, now abandoned.

FIELD OF THE INVENTION

The present invention broadly concerns devices for use in spinal implant systems, particularly those using spinal rods contoured for connection at various locations along the length of the spinal column. More specifically, the invention concerns an apparatus for linking adjacent spinal rods in a top-loading and top-tightening fashion. This invention is particularly useful with methods and devices for posterior fixation of the spine.

BACKGROUND OF THE INVENTION

Several techniques and systems have been developed for use in correcting and stabilizing spinal curvatures, and for facilitating spinal fusion in the case of spinal disorders or degenerative conditions. Typically, a pair of bendable rods are longitudinally disposed adjacent the vertebral column and are fixed to various vertebrae along the length of the spine by way of a number of fixation elements, such as hooks and screws.

Numerous spinal rod systems have been developed which provide transverse connectors for linking the adjacent spinal rods across the spinal midline to provide a rigid and stable construct. Most of these systems present one or more difficulties for spinal surgeons. Many of the devices are high profile which increases soft tissue trauma and surgical complications. Furthermore, in many of these prior systems the attachment mechanisms must be preloaded on the spinal rods which can require significant pre-operative planning and which virtually eliminates the opportunity to add connectors in situ.

One transverse connector system is the TSRH® CROSSLINK® of Danek Medical, Inc. The TSRH® CROSSLINK® utilizes a three point shear clamp mechanism which restricts motion between the rods in all directions, and particularly resists axial forces between rods and torsional moments about the axis of the rods. A quadrilateral construct is formed by laterally connecting the rods across the sagittal plane with rigid plates. The lateral connection reduces the loss of correction that can occur over time.

Rigid transverse connections between spinal rods are beneficial because they restrict rod migration and increase construct stiffness. In many cases involving multi-level fusion of the spine, these features are essential while solid bone fusion is accomplished. In the post-operative period before fusion occurs, a significant amount of motion can occur between the rods, wires and hooks, which can, for example, allow a scoliotic correction to decrease or the pelvis to de-rotate toward its previous, deformed position. By providing a rigid transverse connection between two spinal rods, the loss of correction can be reduced and a stiffer construct can be created which may enhance the promotion of a solid fusion. While the TSRH® CROSSLINK® provides an excellent construct, a need has remained for low profile devices which link adjacent spinal rods in a top-loading and top-tightening fashion with a minimum of components and steps.

SUMMARY OF THE INVENTION

In accordance with one aspect of the invention, a connector is provided for linking adjacent longitudinal members, such as spinal rods, engaged to a spine. The apparatus includes a bridge member sized to span at least a portion of the distance between the spinal rods. A pair of engaging members are connected to the bridge member, each including a receptacle configured to receive a longitudinal member when the connector is disposed over the adjacent rods. The engaging members also include a fixation surface adjacent to the receptacle and configured for engaging a longitudinal member, and a thru-hole defined in the engaging member adjacent to the receptacle for receiving a wedge member. The thru-hole intersects the receptacle and is aligned at an angle such that as the wedge member is advanced through the thru-hole, the wedge member will bear against a rod initially disposed in the receptacle and push the rod against the fixation surface to engage the connector to the rod.

In one specific embodiment of the invention, the engaging members include an elongated connecting portion which is received by a bore in the bridge member. The bridge member also includes a pair of engaging surfaces adjacent to and contiguous with a respective one of the bores for engaging a connecting portion. A second thru-hole defined in the bridge member intersects each one of the bores and is aligned at an angle such that as a wedge member is advanced through the second thru-hole, the wedge member will bear against the connecting portions and push each one against a corresponding one of the engaging surfaces.

In another specific embodiment, the bridge member defines a slot for receiving one of the connecting portions and a first fastener bore which intersects the slot. The connecting portion also defines a second fastener bore which is alignable with the first fastener bore of the bridge member when the connecting portion is inserted into the slot.

In some embodiments of this invention, the fixation surface includes a circular concavity which has a smaller radius than the radius of the longitudinal member. This provides three points of contact on each of the longitudinal members which restricts motion between the rods in all directions.

One object of the invention is to provide an apparatus for use in laterally connecting longitudinal members implanted adjacent a patient's vertebral column. Another object of this invention is to provide an apparatus which restricts rod migration and increases overall construct rigidity.

One advantage of a preferred embodiment of this invention is that it provides fixation assemblies that can be top loaded, or implanted over spinal rods after the spinal rods have been engaged to the spinal column. A further benefit is achieved by top-tightening aspects of the invention.

Another benefit of this invention is that a preferred embodiment provides three points of contact on the spinal rod which restricts rod migration and increases overall construct rigidity.

Other objects and further benefits of the present invention will become apparent to persons of ordinary skill in the art from the following written description and accompanying figures.

BRIEF DESCRIPTION OF THE DRAWINGS

FIG. 13 is a top elevational view of an adjustable transverse connector.

FIG. 14 is a side elevational view of the transverse connector of FIG. 13.

FIG. 15 is a cross-sectional view of the connector of FIG. 13 taken along lines 15—15.

FIG. 18 is a side elevational view of an alternative embodiment of the transverse connector having shortened connecting portions.

FIG. 23A is a perspective view of another adjustable connector according to this invention in an extended configuration.

FIG. 23B is a perspective view of the adjustable connector of FIG. 23A in a closed configuration.

DESCRIPTION OF THE PREFERRED EMBODIMENTS

Figure 1:
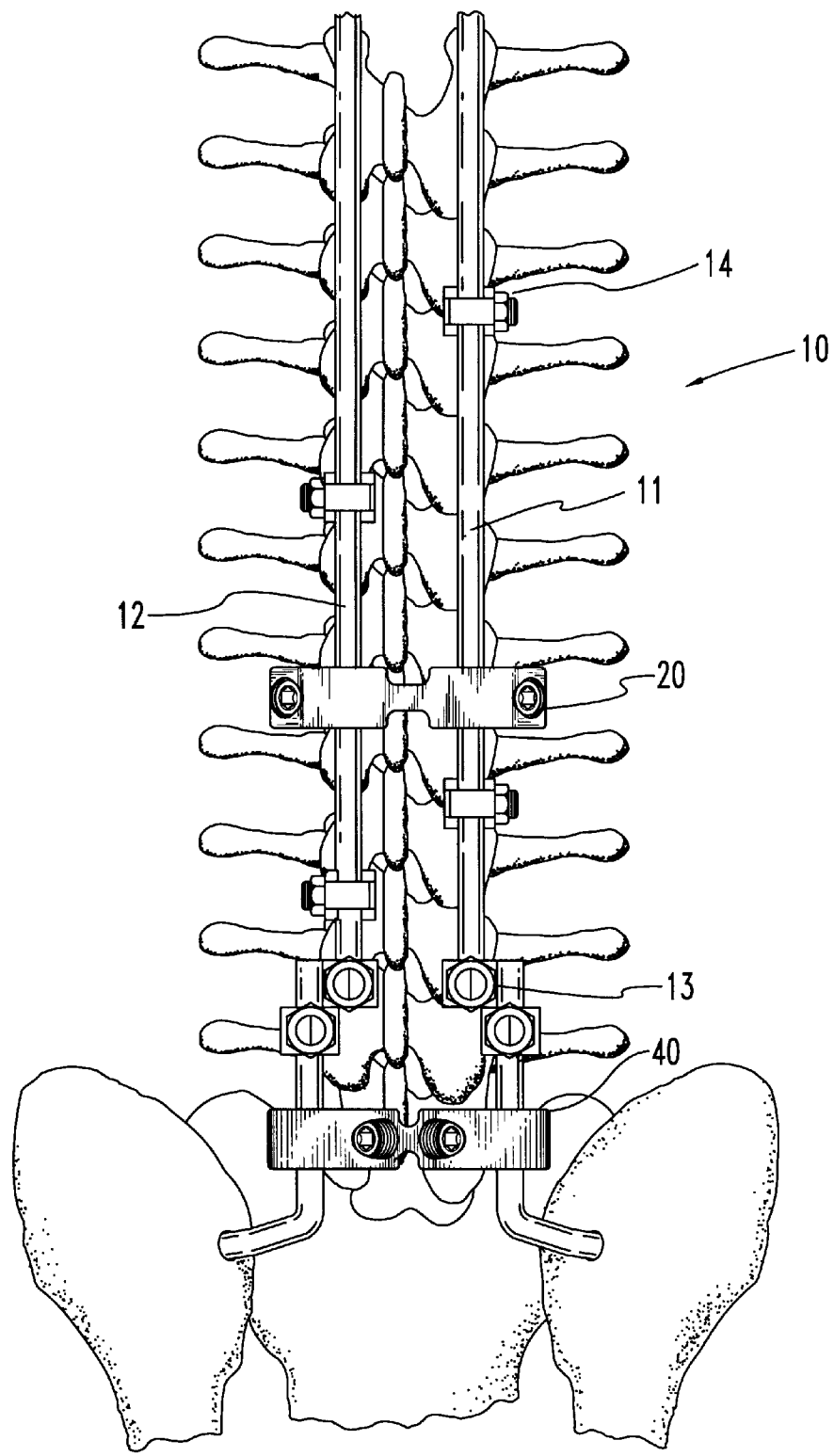
FIG. 1 is a top elevational view of a spinal fixation system engaged to a spine according to one aspect of this invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention is useful for posterior internal fixation of the spine which is indicated for correcting and stabilizing spinal curvatures and for facilitating spinal fusion in the case of spinal disorders or degenerative conditions. This invention provides a top-loaded, top-tightening, low profile posterior fixation system which requires minimal instrumentation yet provides a stable, rigid quadrilateral construct that restricts rod migration and increases overall construct rigidity.

Figure 2:
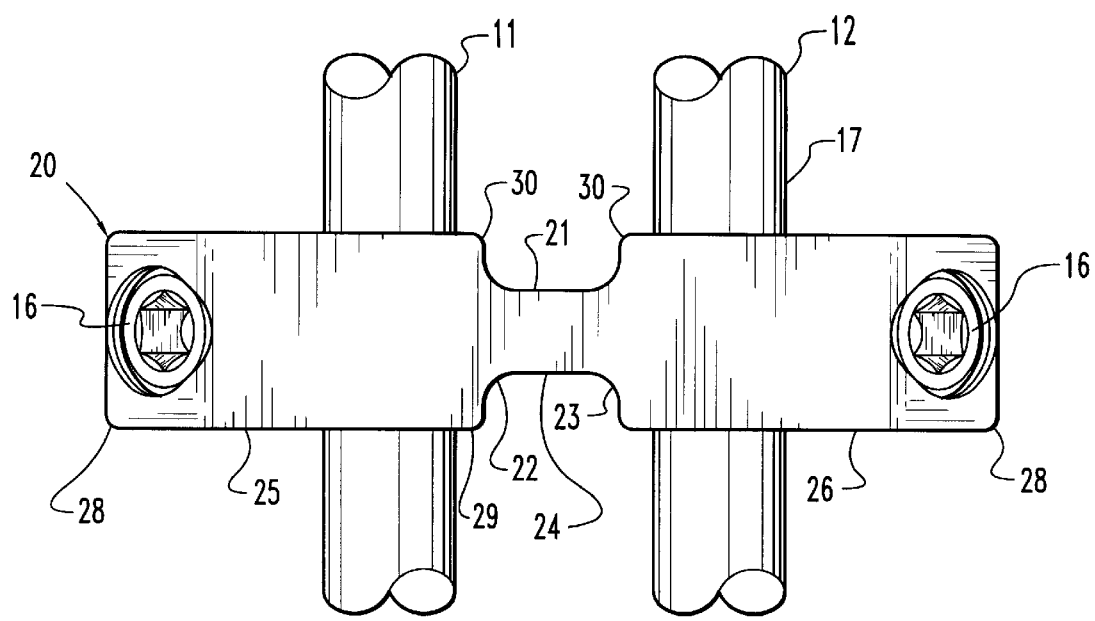
FIG. 2 is a top elevational view of a transverse connector engaged to spinal rods wherein the engaging members are disposed medially and the thru-holes are disposed laterally on the connector.
Figure 3:
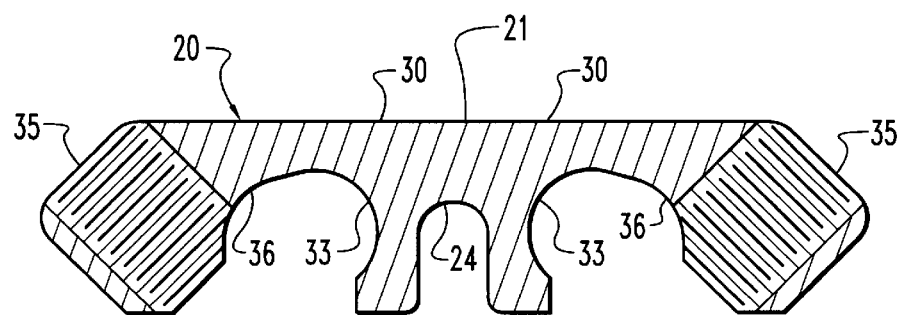
FIG. 3 is a cross-section of the transverse connector of FIG. 2.

A spinal fixation system 10 in accordance with one preferred embodiment of the present invention is depicted in FIGS. 1–3. The system 10 includes a pair of longitudinal members, preferably spinal rods, 11,12 means for engaging the longitudinal members to the vertebral column, 13, 14, a pair of wedge members 16 and a connector 20 configured to span a distance between the rods 11, 12 when the rods 11, 12 are engaged to the spine.

As shown more clearly in FIGS. 2 and 3, the connector 20 includes a pair of engaging members 25, 26 each defining a fixation surface 33 at a corresponding first end 28 thereof. The connector 20 also includes a connecting surface 30 at a second end 29 of each engaging member 25, 26. A bridge member 21 includes a first end 22 and a second end 23 which are attached to the connecting surfaces 30 of each of the rod engaging members 25, 26. The bridge member 21 preferably includes a reduced width and depth portion 24 to avoid the laminae and spinous process remnant during the surgical procedure. The reduced portion 24 also provides means for contouring or bending the connector 20 as needed to conform to the spinal anatomy of the patient.

Each of the engaging members 25, 26 further defines a receptable 36 for receiving a spinal rod therein and a first thru-hole 35 for receiving a wedge member 16. The thru-holes 35 intersect the corresponding receptacles 36 and are aligned so that when a wedge member 16 is advanced through the thru-hole 35, the wedge member 16 bears on a corresponding rod 11, 12 within a receptacle 36 to force the rod 11, 12 into contact with an opposite fixation surface 33 to engage the rod to the connector. In one specific embodiment, the engaging members 25, 26 are integrally attached to the bridge member 21. In one embodiment, the thru-holes 35 are threaded.

One advantage of this invention is that it provides connectors that can be top loaded, or implanted over spinal rods after the spinal rods have been engaged to the vertebrae. Top-loading is advantageous because it reduces the required size of the surgical opening and resulting trauma to the patient, and because it greatly simplifies the surgical implantation. Top-loading also provides a mechanical advantage during implantation of the system in that the connector 20 can be easily placed over adjacent rods 11, 12 and then the rods 11, 12 can be locked laterally relative to each other by tightening the wedge members 16.

Figure 4:
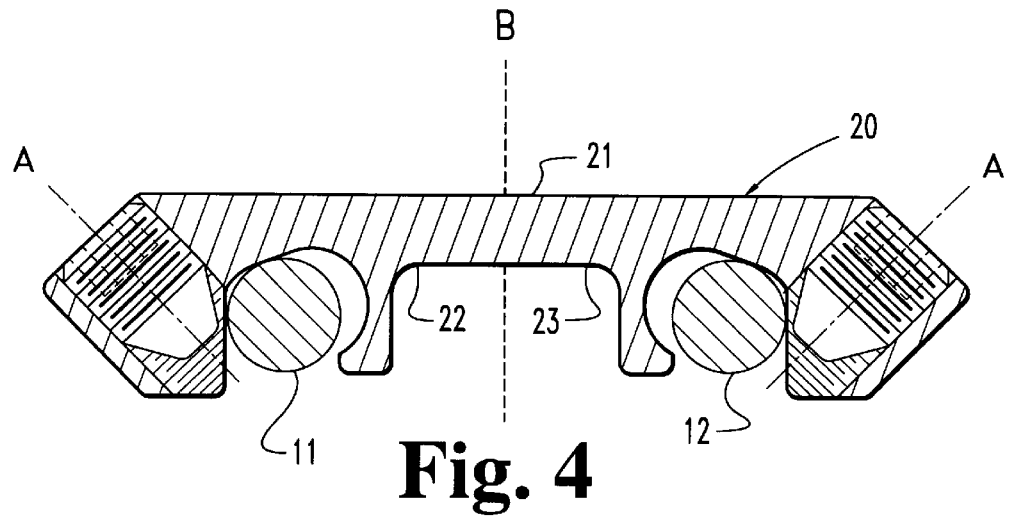
FIG. 4 is a cross-sectional view of the transverse connector of FIG. 2 which is top loaded over two spinal rods.
Figure 5:
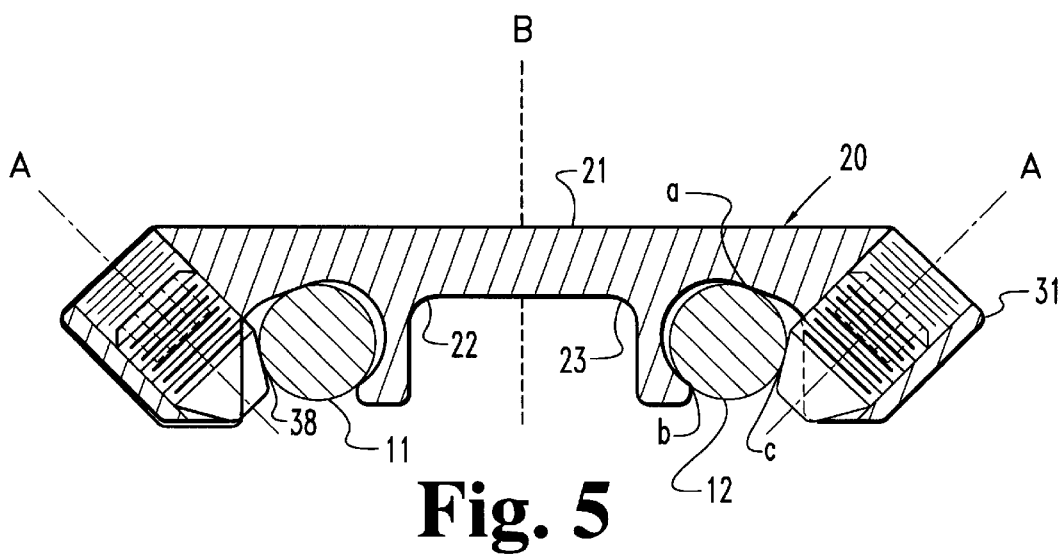
FIG. 5 is a cross-sectional view of the transverse connector of FIG. 2 engaged to two spinal rods.

Referring to FIGS. 3, 4 and 5, the connector 20 can be disposed or loaded over longitudinal members or rods 11, 12 which have been previously engaged to the spine such that the rods 11, 12 are received into the receptacle 36 of the connector 20. Then, as a wedge member 16 is advanced through a thru-hole 35, the wedge member 16 pushes the rod 11 against the fixation surface 33. Preferably, the fixation surface 33 is a circular concavity which has a smaller radius than the radius of the rod 11, 12. This configuration provides three points of contact a, b, c on the longitudinal members 11, 12 as shown in FIG. 5. Two points of contact a and b are provided by the fixation surface 33, and the third point of contact c is provided by bearing surface 38 on the wedge member 16.

Figure 7:
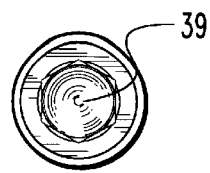
FIG. 7 is a top elevational view of a set screw.
Figure 6:
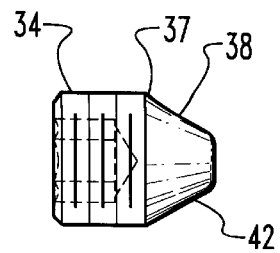
FIG. 6 is a side elevational view of a set screw.

As shown more clearly in FIGS. 6 and 7, the wedge member 16 is preferably a set screw 37 which has a bearing surface 38 and an internal hex 39 to accept a conventional driving tool. Most preferably, the head 34 of the wedge member 16 or set screw 37 is configured to rest entirely within the thru-hole 35. In this manner, the set screw 37 can be situated so that it does not extend above the upper surface 31 of the connector 20 when the set screw 37 is fully advanced in the thru-hole 35 and bearing against a rod 12 as shown in FIG. 5. In the case of a threaded set screw 37, the thru-holes 35 carry corresponding female threads. Preferably, bearing surface 38 is shaped to conform to an outer surface 17 of a rod 11, 12. The outer surface 17 of the rod 11, 12 is typically circular, but can be of any suitable shape. The bearing surface 38 is preferably a tapered tip 42.

Referring to FIGS. 2 through 5, the bridge members defines an axis B between the first end 22 and the second end 23 of the bridge member 21. The thru-holes 35 are preferably oriented at an angle A of less than 90° relative to the axis B of the bridge member 21. Any angle which allows the wedge member 16 to bear against a rod 11, 12 in the receptacle 36 and push the rod 11, 12 against the fixation surface 33 so that the adjacent rods 11, 12 are retained in a desired special relationship are contemplated. Such angles include but are not limited to angles of about 40°, 45° and 60°. Preferably the angle is established to preserve the top-tightening aspect of the invention, which can help reduce the size of the surgical site for implantation.

Figure 8:
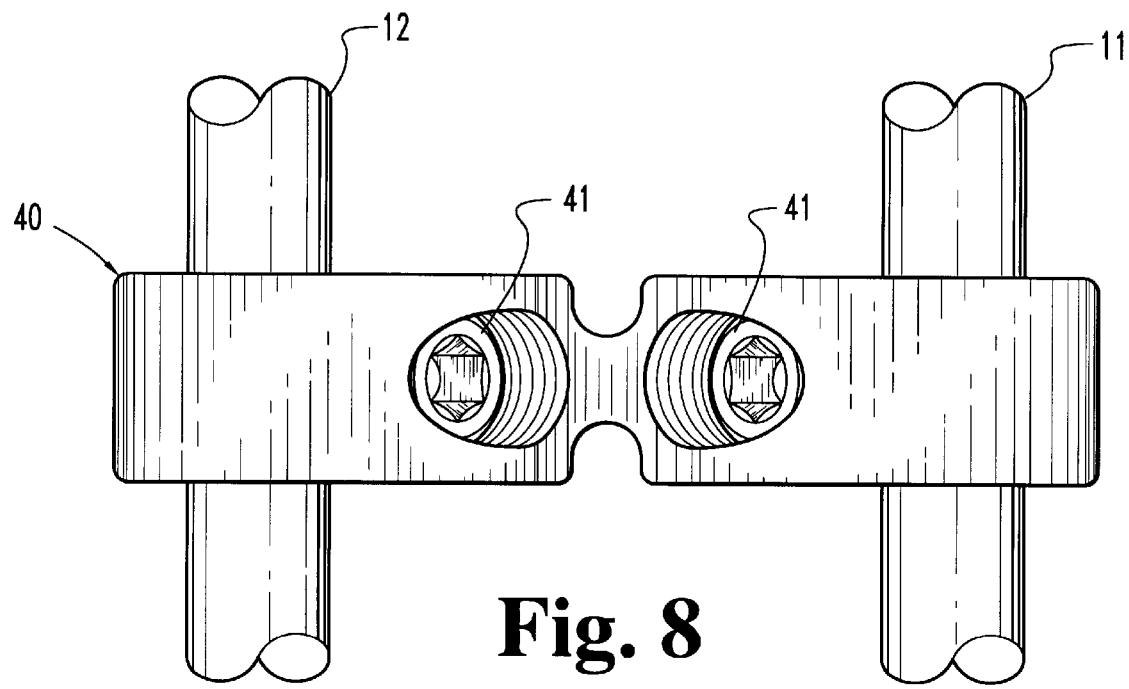
FIG. 8 is a top elevational view of a transverse connector similar to FIG. 1 except that the engaging members are disposed laterally and the thru-holes are disposed medially on the connector.
Figure 9:
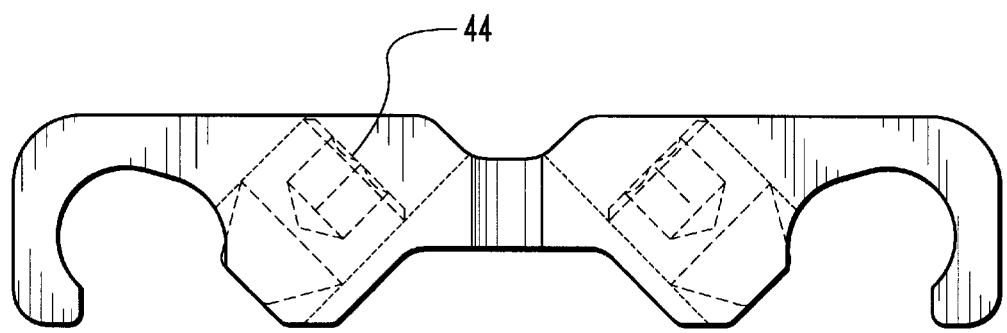
FIG. 9 is a side elevational view of the transverse connector of FIG. 8.

In the embodiments shown in FIGS. 1 through 5, the connector 20 includes thru-holes 35 which are disposed laterally on the connector, i.e., laterally outboard from the axis B. In this configuration the thru-holes 35, and therefore the wedge members 16, act toward the axis B. Alternatively, the first thru-holes 44 may be disposed medially on the connector 40, as shown in FIGS. 8 and 9. This embodiment is desirable when the span between the longitudinal members 11, 12 is sufficient to accommodate both wedge members 41. A transverse connector 20 which utilizes laterally disposed wedge members 16 such as depicted in FIGS. 1–5, can be used when the span between the longitudinal members 11 and 12 is smaller than about 1⅛" (28 mm). However, when appropriate, the medial connector embodiment 40 is desirable because it permits a smaller surgical site and allows easier access to the wedge members 41 with tools (not shown) for engaging the wedge member 41 during the surgical procedure.

Figure 10:
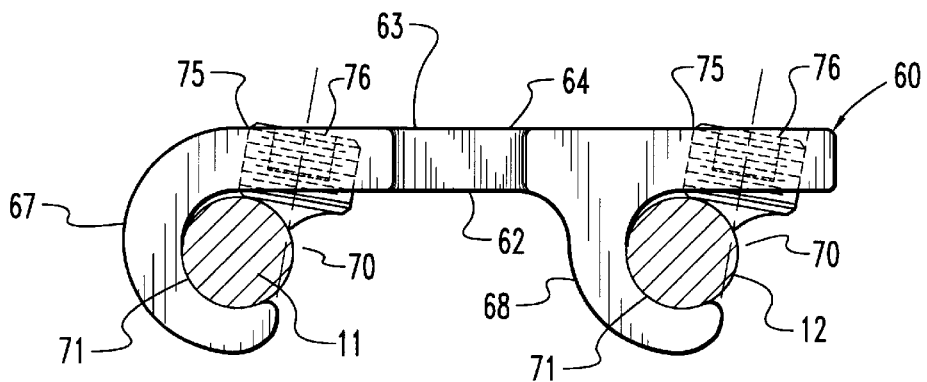
FIG. 10 is a side elevational view of an alternative embodiment of a transverse connector.

Referring to FIG. 10, this invention also contemplates a C-clamp shaped connector 60. The C-clamp connector 60 also includes a bridge member 62 which spans between a pair of engaging members 67, 68. The bridge member 62 is connected to each of the engaging members 67, 68 at a first end 63 and a second end 64 of the bridge member 62. A pair of receptacles 70 on the connector 60 are configured to receive longitudinal members or rods 11, 12. A first thru-hole 75 is defined in each of the engaging members 67, 68. The thru-holes 75 intersect the corresponding receptacles 70 and are aligned at an angle such that as a wedge member 76 is advanced through the thru-hole 75, the wedge member 76 will bear against the longitudinal member 11, 12 and push the longitudinal member 11, 12 against a fixation surface 71 adjacent to the corresponding receptacles 70 to engage the connector 60 to a longitudinal member 11, 12. Like the previous embodiments, the connector 60 can be loaded over a pair of spinal rods 11, 12, with the rods 11, 12 initially in contact with only the receptacles 70 or the underside of the connector 60. The connector can be manually shifted until the rods contact the fixation surfaces 72. Final engagement is accomplished by tightening the wedge members 76 against the rods.

Figure 11:
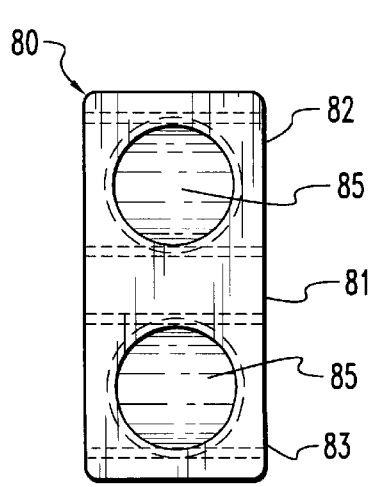
FIG. 11 is a top elevational view of a closed transverse connector embodiment.
Figure 12:
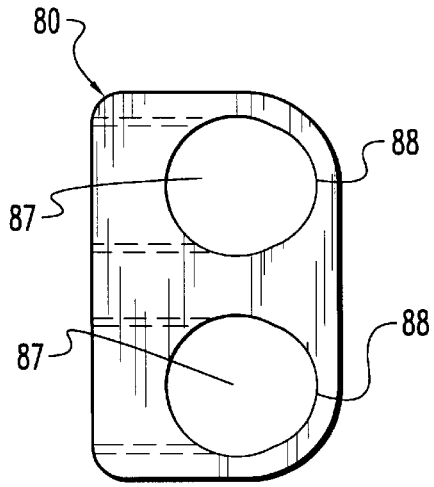
FIG. 12 is a side elevational view of the transverse connector of FIG. 11.

Closed connector embodiments are also contemplated by this invention as shown in FIGS. 11 and 12. In one embodiment, the closed connector 80 must be preloaded on the longitudinal members 11, 12 before the longitudinal members 11, 12 are engaged to a spinal column. The closed connector 80 includes a bridge member 81 attached to a pair of engaging members 82, 83. A pair of rod receptacles 87 are configured to receive a longitudinal member 11, 12. A first thru-hole 85 is defined in each engaging member 82, 83 for receiving a wedge member 16. As the wedge member 16 is advanced through the thru-hole 85, the wedge member 16 will bear against a longitudinal member 11, 12 in the receptacle 87 and push the longitudinal member 11, 12 against a fixation surface 88 to engage the connector 80 to the longitudinal member 11, 12. Preferably the fixation surface 88 is a circular concavity which has a smaller radius than the radius of the longitudinal member 11, 12, thus providing three points of contact as described above.

Another aspect of this invention provides means for adjusting the distance between the longitudinal members 11, 12 while still retaining the top-loaded and top-tightening aspects of the invention. FIGS. 13 and 14 show an adjustable transverse connector 90. The connector 90 includes a bridge member 91 having a first end 92, a second end 93 and engaging members 94, 95. The engaging members 94, 95 each include an engaging portion 96 which define thru-holes 99 and which are engageable to the longitudinal members 11, 12 as described above. Each engaging member 94, 95 also includes elongated connecting portions 97, 98 sized to span at least a portion of the distance between the adjacent longitudinal members or rods 11, 12. The bridge member 91 defines a pair of bores 101, each for receiving a corresponding one of the elongated connecting portions 97, 98. The bridge member also includes a pair of engaging surfaces 102 which are adjacent to and contiguous with a respective one of the bores 101 for engaging the corresponding connecting portions 97,98, as shown in FIG. 15. A pair of second thru-holes 105 are defined in the bridge member 91 for receiving wedge members 106. A second thru-hole 105 intersects each of the bores 101 and is aligned at an angle such that as the wedge member 106 is advanced through the second thru-hole 105, the wedge member 106 will bear against the corresponding connecting portion 97, 98 and push each of the connecting portions 97, 98 against a corresponding one of the engaging surfaces 102. Preferably, the engaging surfaces 102 include a circular concavity which has a smaller radius than a radius of the bore 101 and of the circular connecting portions 97, 98.

Figure 16:
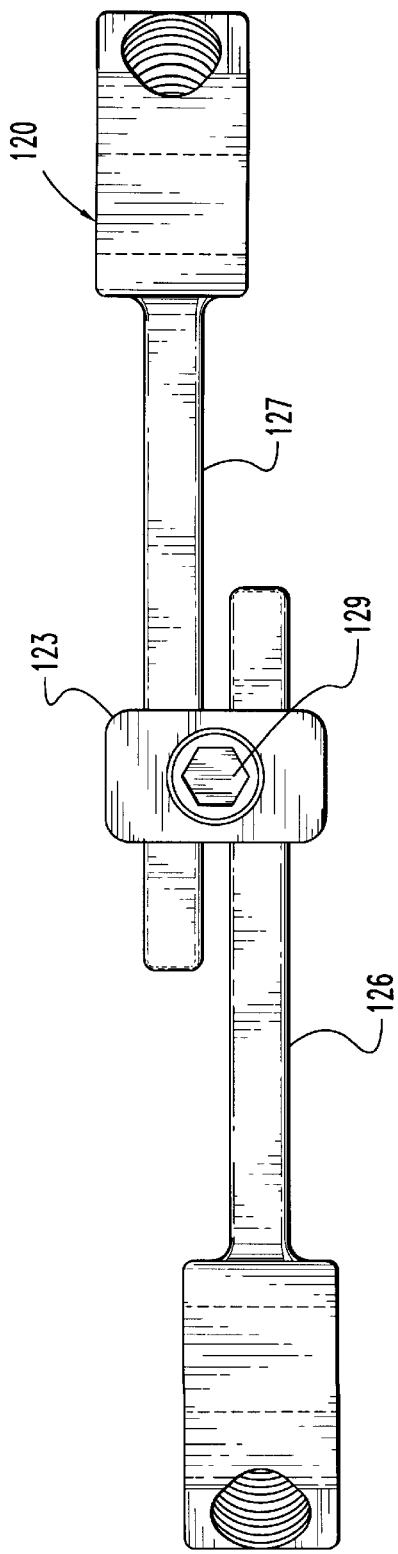
FIG. 16 is a top elevational view of another adjustable transverse connector.
Figure 17:
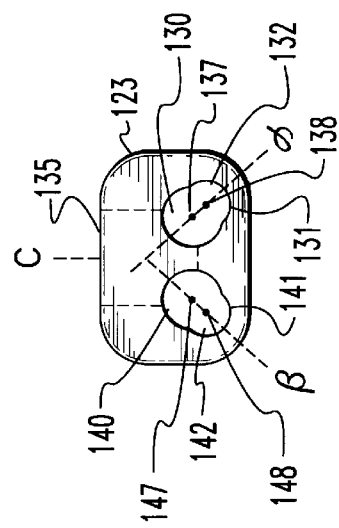
FIG. 17 is a side elevational view of the bridge member of the transverse connector shown in FIG. 16.

One preferred embodiment of an adjustable transverse connector 120 which is similar to the embodiment shown in FIGS. 13–15 is shown in FIGS. 16 and 17. A single second thru-hole 135 defined in the bridge member 123 intersects both of the bores 130, 140 so that a single wedge member 129 engages both of the connecting portions 126, 127 as shown in FIGS. 16 and 17. According to this embodiment, a single wedge member 129 forces the connecting portions 126 and 127 laterally into the respective engaging surfaces 131, 141. Each engaging surface 131, 141 includes a concavity 142, 132 which has a centroid 138, 148. As shown in FIG. 17, a line between the centroid 137 of a bore 130 and the centroid 138, of its corresponding adjacent concavity 132 and a line B between the centroid 147 of the other bore 140 and the centroid 148 of its corresponding adjacent concavity 142 diverge away from the second thru-hole 135. In this configuration, as the wedge member 129 is advanced through the second thru-hole 135 the connecting portions 126, 127 are pushed away from the axis C of the second thru-hole 135. The connecting portions 126, 127 are thus engaged to the corresponding engaging surfaces 131, 141 with a single wedge member 129.

In order to provide a broad range of connectors to address a variety of spinal situations and vertebral levels, connectors of various sizes are contemplated. For example, the connector 110 shown in FIG. 18 provides shortened connecting portions 112 connected to a bridge member 111.

The invention also includes telescoping adjustable transverse connector embodiments as shown in FIGS. 19 through 30. In one specific embodiment depicted in FIGS. 19–21, a telescoping adjustable transverse connector 150 includes a bridge member 152 connected to a first engaging member 155 and a second engaging member 162, each having a respective first end 156, 163 and second end 158, 165. The engaging members 155, 162 each include fixation portions 157, 164 at the first end 156, 163. The fixation portions 157, 164 each include receptacles 168, 169 and fixation surfaces 170, 171. The receptacles 168, 169 are each intersected with a first thru-hole 175 for receiving a wedge member 241. The thru-holes 175 are aligned so that when a corresponding wedge member is advanced through the thru-hole 175, the bearing surface 242 of the wedge member 241 bears on a corresponding longitudinal member within the receptable 168, 169 to force the longitudinal member into contact with the corresponding fixation surface 170, 171. In one embodiment, the thru-holes 175 are threaded.

Figure 20:
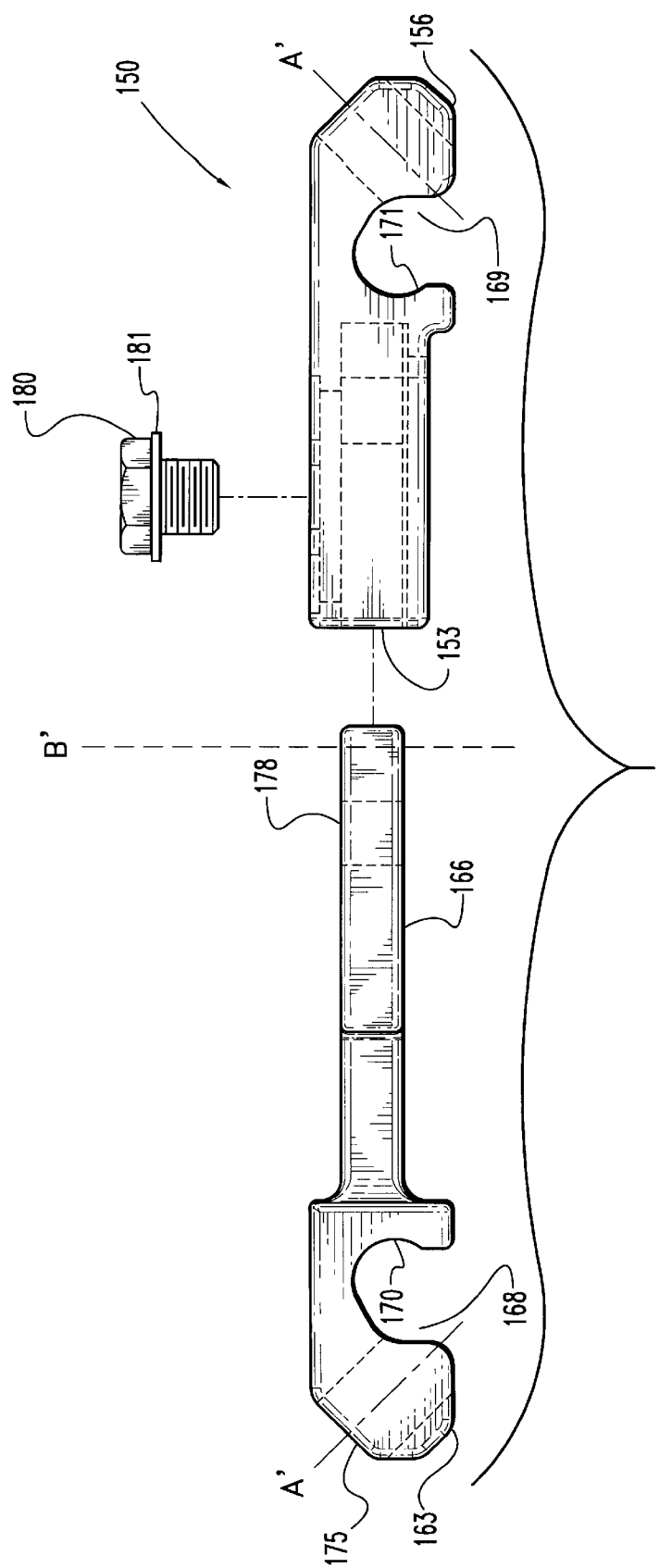
FIG. 20 is a side elevational view of the transverse connector shown in FIG. 19.

The fixation portions 157, 164 of the connector 150 are engageable to longitudinal members in a top loaded fashion in the manner described above. Referring to FIG. 20, the device defines an axis B' between the first ends 156 and 163. The thru-holes 175 are preferably oriented at an angle A' of less than 90° relative to the axis B'. Of course, any angle is contemplated which allows a wedge member to bear against a longitudinal member in one of the receptacles 168 or 169 and push the longitudinal member against the corresponding fixation surface 170 or 171, respectively, so that the longitudinal member is retained in a desired special relationship. Such angles include but are not limited to angles of about 40°, 45° and 60°. Preferably the angle is established to preserve the top-tightening aspect of the invention, which can help reduce the size of the surgical site for implantation.

In the embodiments shown in FIGS. 19 through 22, the connector 150 includes thru-holes 175 which are disposed laterally on the connector, i.e., laterally outboard from the axis B'. In this configuration the thru-holes 175, and therefore the wedge members, act toward the axis B'. Alternatively, the thru-holes may be disposed medially on a connector 200, such as thru holes 225 as shown in FIGS. 23A through 30. This embodiment is desirable when the span between the longitudinal members is sufficient to accommodate both wedge members 241. A transverse connector 150 which defines laterally disposed thru-holes 175 such as depicted in FIGS. 19–22, can be used when the span between the longitudinal members need to be smaller than about 1⅛" (28 mm). However, when appropriate, a medial connector embodiment 200 is desirable because it permits a smaller surgical site and allows easier access to the wedge members 241 with tools (not shown) for engaging the wedge members 241 during the surgical procedure.

Figure 24A:
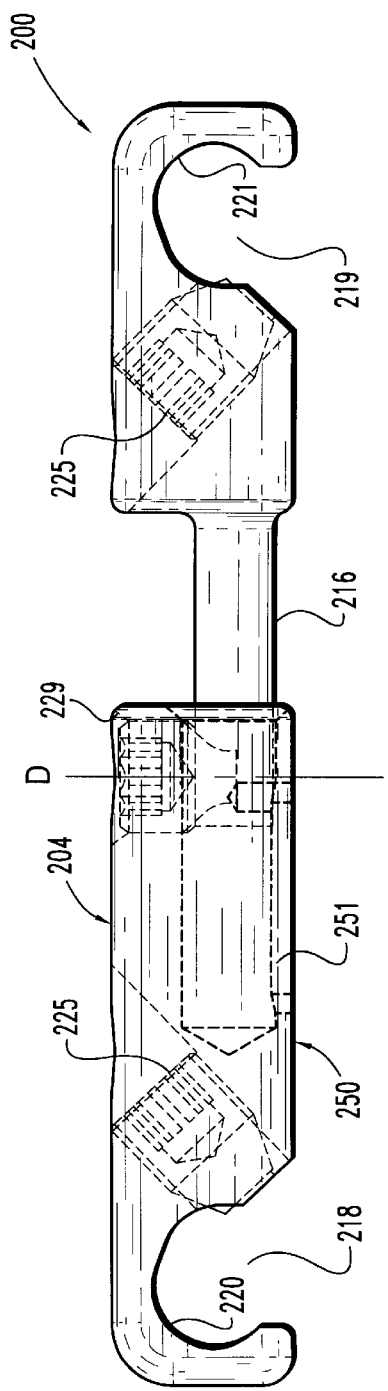
FIG. 24A is a side elevational view of the connector shown in FIG. 23A.
Figure 24B:
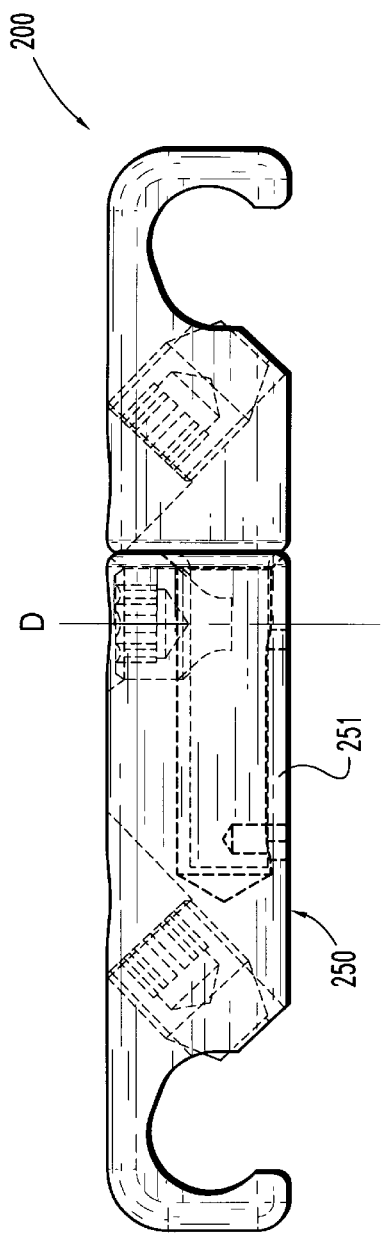
FIG. 24B is a side elevational view of the connector shown in FIG. 23B.
Figure 25:
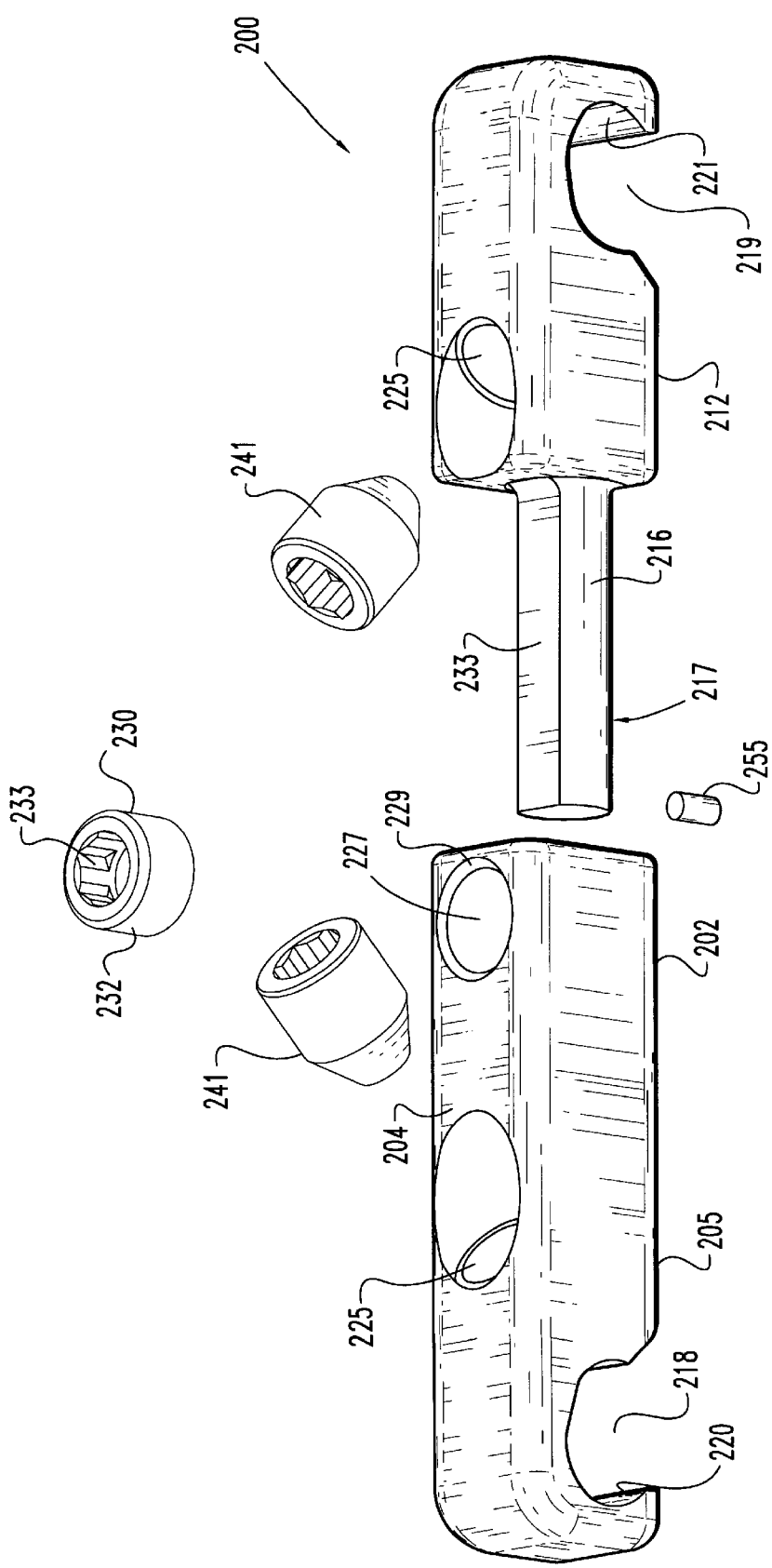
FIG. 25 is an exploded perspective view of the connector shown in FIGS. 23 and 24.

The first engaging member 155, 205 of the connectors 150, 200 shown in FIGS. 19–30 include a first connecting portion 159, 209 at the second end 158, 208. The second engaging members 162, 212 of these connectors 150, 200 similarly include a second connecting portion 166, 216 at the second ends 165, 215. The bridge member 152, 202 of the connectors 150, 200 each define a slot 153, 203 for receiving a second connecting portion 166, 216. The first connecting portion 159, 209 of the first engaging member 155, 205 is preferably integrally attached to the bridge member 152, 202. The bridge member 152, 202 also preferably defines a first fastener bore 177, 227. (FIG. 25)

Figure 19:
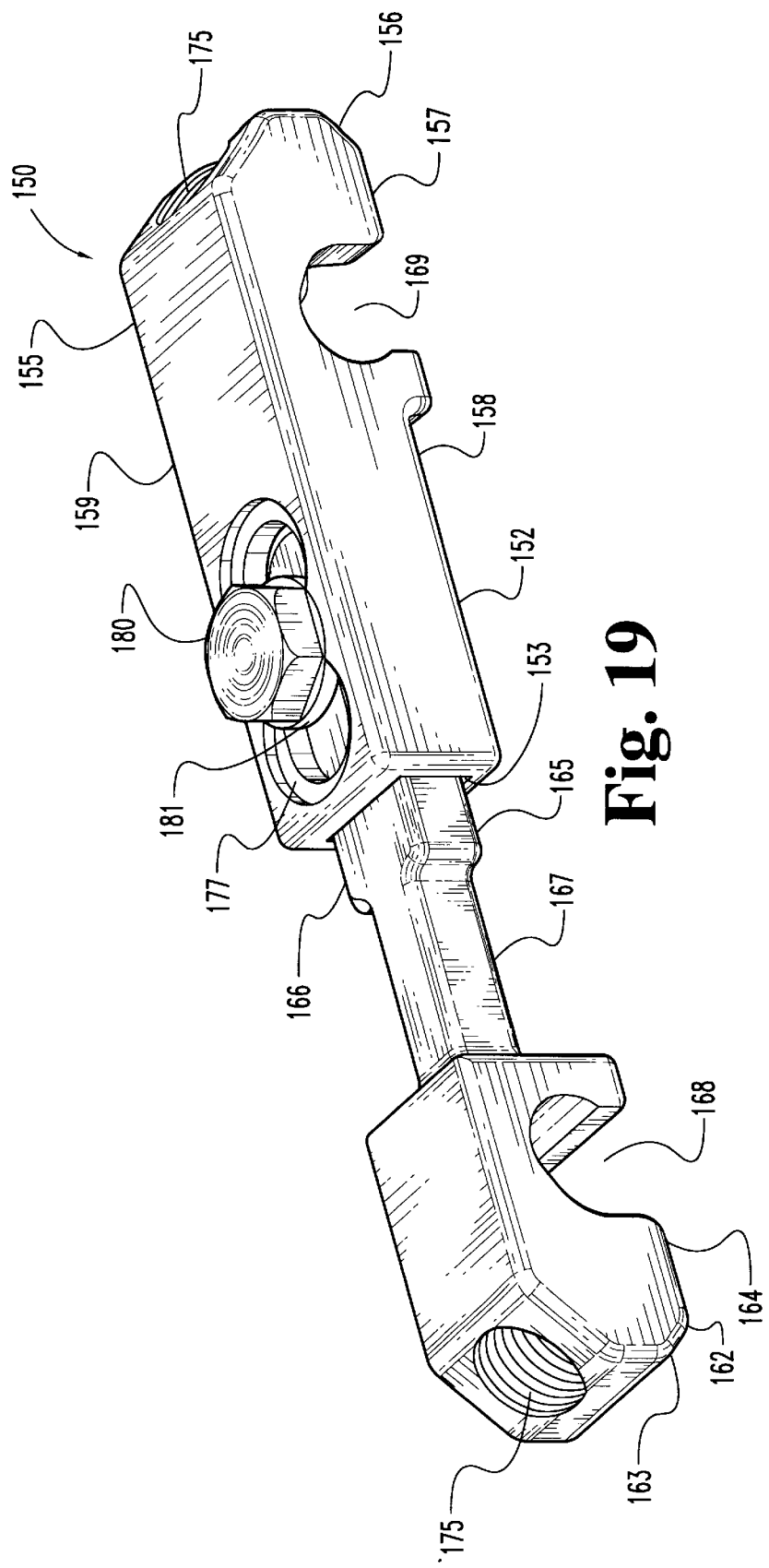
FIG. 19 is a perspective view of still another adjustable transverse connector according to this invention.
Figure 21:
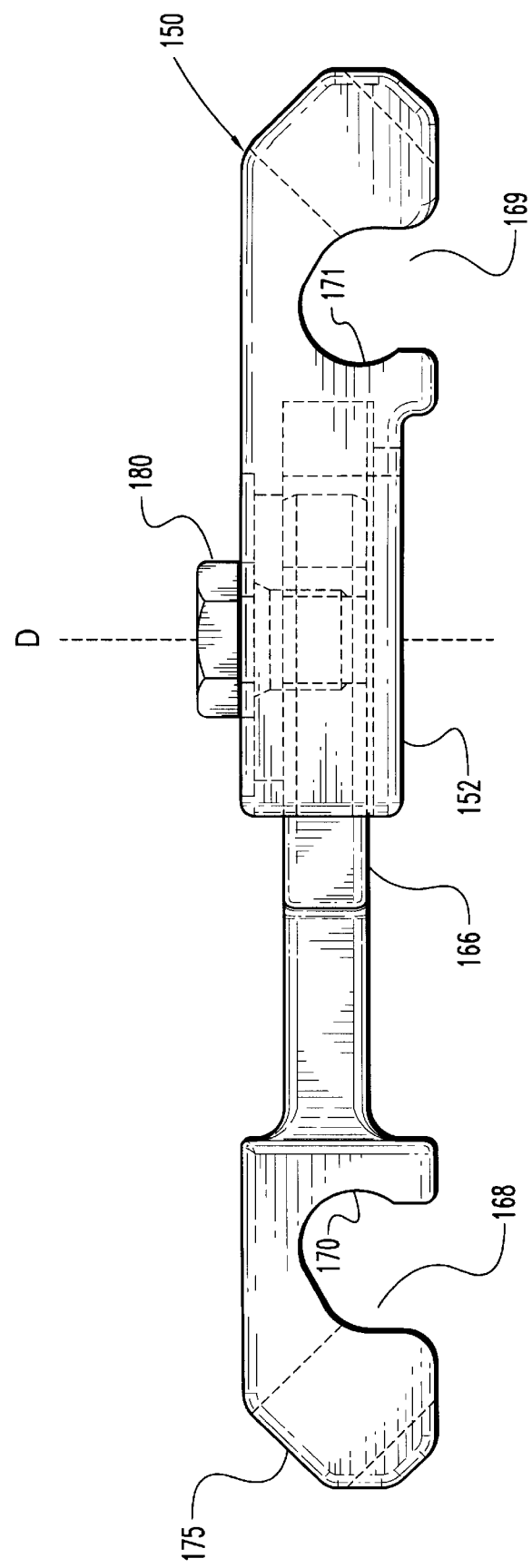
FIG. 21 is an exploded side view of the transverse connector of FIG. 19.

Referring to the lateral outboard connector embodiment of FIGS. 19–21, the axis D of the first fastener bore 177 intersects the slot 153 for receiving a fastener 180 to connect the second connecting portion 166 to the bridge member 152. The second connecting portion 166 defines a second fastener bore 178. The second fastener bore 178 is alignable with the first fastener bore 177 when the second connecting portion 166 is inserted in the slot 153. A fastener 180 is extendable through each of the first and second fastener bores 177, 178 to clamp the second connecting portion 166 to the bridge member 152. Any suitable fastener is contemplated, including but not limited to a hex head screw 180 with an integral washer 181. The fastener may also include a locking screw 228 having a circular head 229 with an internal hex recess 230 to receive a driving tool, as shown in FIG. 25.

Figure 22:
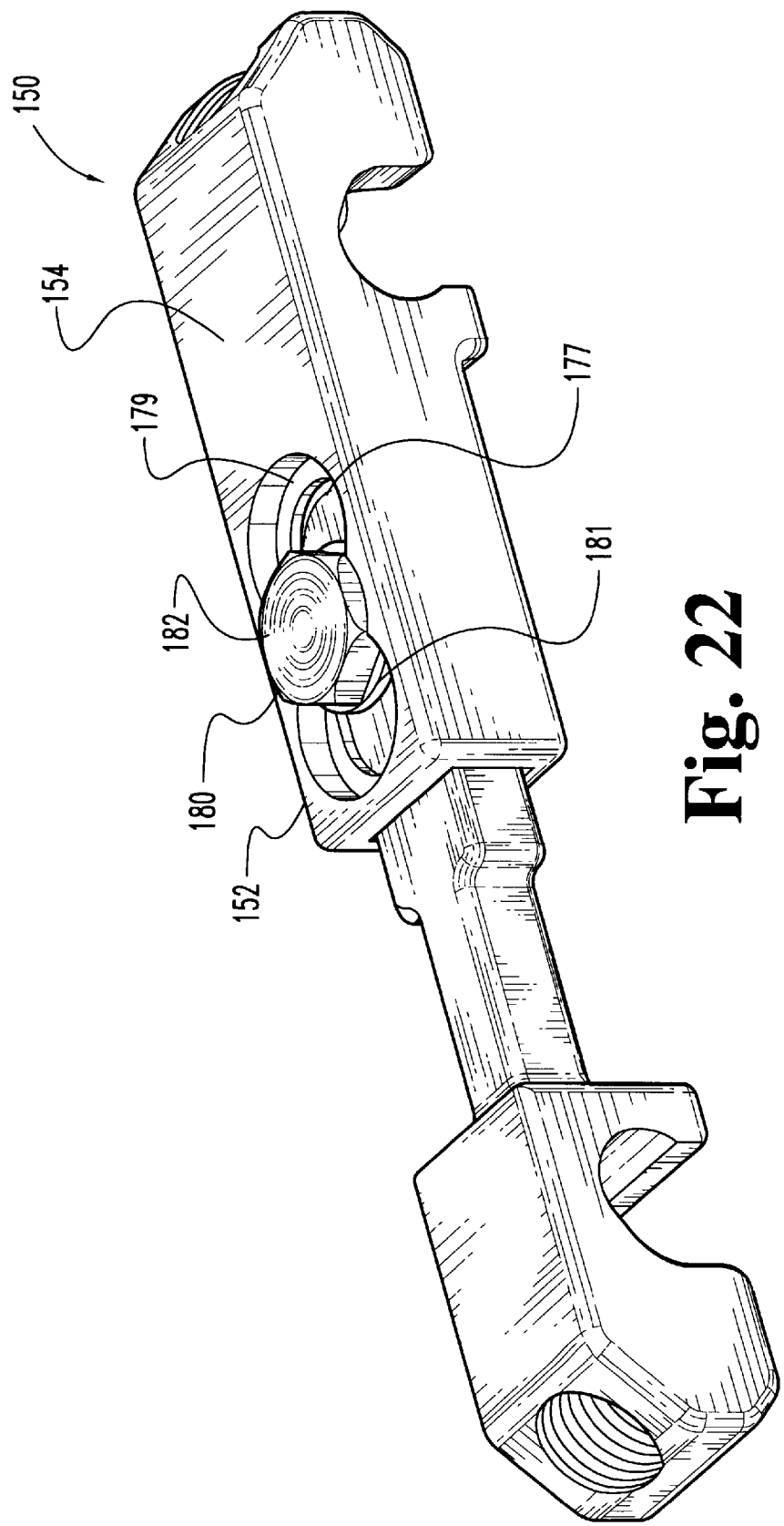
FIG. 22 is a perspective view of still another transverse connector of this invention.

Preferably, the first fastener bore 177, 227 of the bridge member 152, 202 includes a recess 179, 229 defined in an upper surface 154, 204 of the connector 150, 200 as shown in FIGS. 22 and 23A. The head 182, 232 of the fastener 180 can be sized to be received within the recess 179, 229 without extending substantially above the upper surface 154 of the bridge member 152. This embodiment provides a low profile system. A fastener having a circular head 232 and an internal hex 230 such as the locking screw 228 depicted in FIG. 25 is preferred for this configuration.

In one embodiment shown in FIG. 19, the bridge member 152 also includes a number of first fastener bores 177. The second connecting portion 166 is slidable within the slot 153 so that the second fastener bore 178 is alignable with each of the number of first fastener bores 177. This configuration allows adjustability in the length of the connector 150. In one specific embodiment, the second connecting portion 166 includes an area of reduced width 167 for bending and contouring the connector 150.

Figure 29:
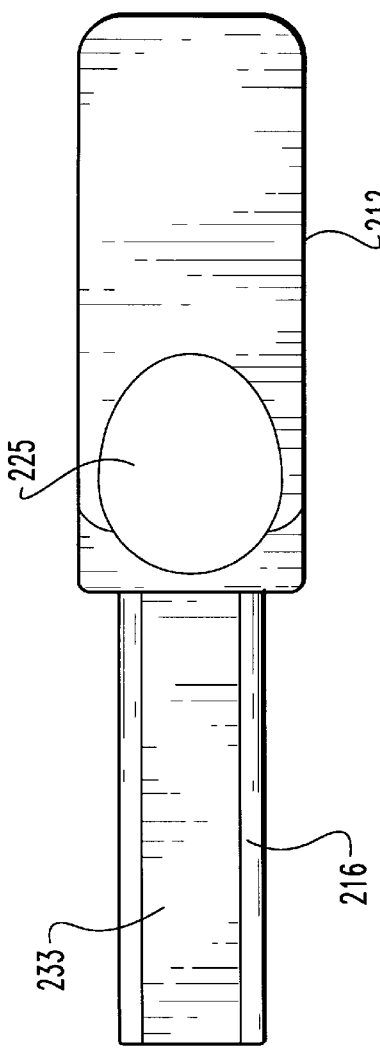
FIG. 29 is a top elevation view of the second engaging member according to one aspect of this invention.
Figure 30:
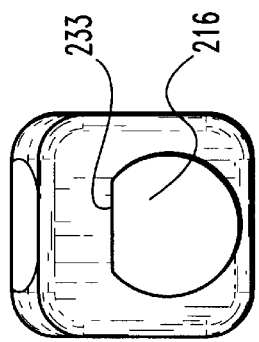
FIG. 30 is a front elevational view of the second engaging member shown in FIG. 29.

In a further specific embodiment depicted in FIGS. 23A–26, the fastener is a locking screw 230 having a flat bearing surface 234. The second connecting portion 216 preferably has a circular cross-section interrupted by a flat upper surface 233 as shown in FIGS. 25 and 29–30. The action of the flat bearing surface 234 of the locking screw 230 on the flat upper surface 233 of the second connecting member 216 locks the first and second engaging members 205 and 212 together and thereby links the adjacent longitudinal member in a desired spatial relationship.

In another specific embodiment, the connectors are provided with provisional connecting means for maintaining the first engaging member 205 and the second engaging member 212 in slidable engagement. The provisional connecting means allows the connector 200 to range from a fully extended length EL as shown in FIGS. 23A, 24A to a fully closed length CL as shown in FIGS. 23B, 24B. This provisional means keeps the first and second engaging members 205, 212 in sliding engagement until the surgeon has top loaded the connector 200 over the longitudinal members and fixed the distance between the first and second engaging members 205, 212 with a fastener, such as lock screw 230. This provisional means reduces fiddle factor because the surgeon is able to adjust the distance between the receptacles 218 and 219 to accommodate the distance between longitudinal members implanted on the spine without having to assemble the connector 200 during the surgery.

Figure 26:
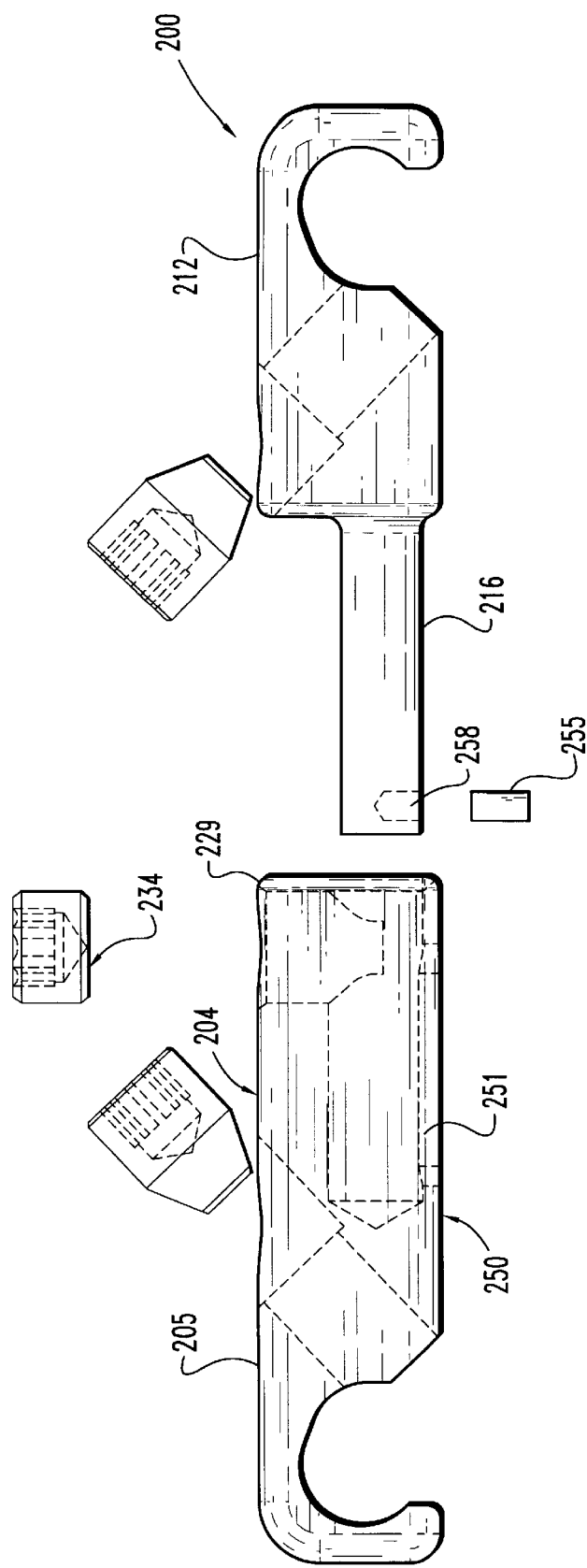
FIG. 26 is an exploded side elevational view of the connector shown in FIGS. 23 and 24.
Figure 27:
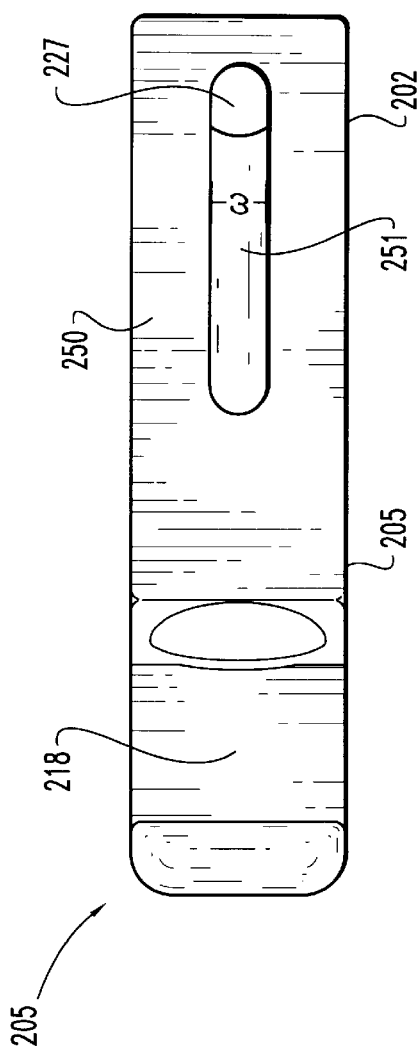
FIG. 27 is a bottom elevational view of the first engaging member and bridge member of the connector shown in FIGS. 23–26.
Figure 28:
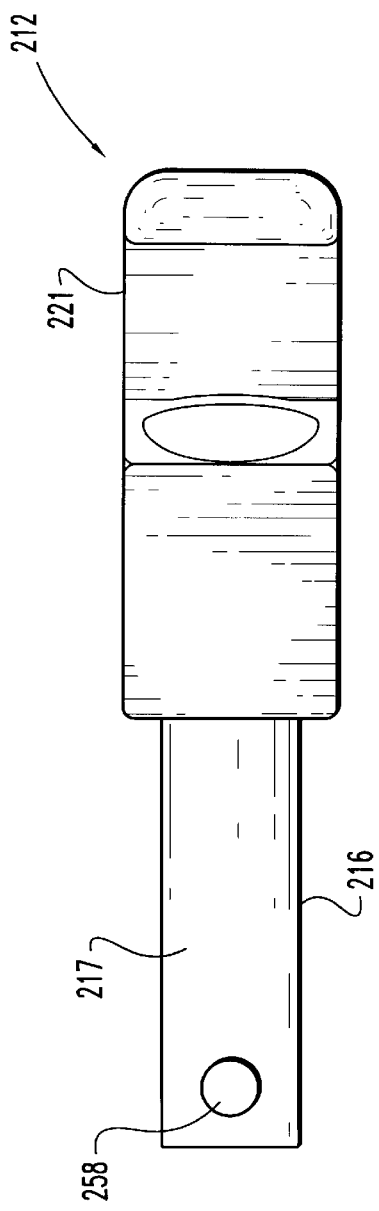
FIG. 28 is a bottom elevational view of the second engaging member of the connector shown in FIGS. 23–26.

The invention contemplates any provisional means which will keep the first and second engaging members 205 and 212 is sliding engagement. In one preferred embodiment, the provisional means includes a pin and groove arrangement. In a specific embodiment, a groove 251 is defined in the lower surface 250 of the bridge member 202 as shown in FIGS. 26 and 27. The groove 251 is of sufficient width that a pin 255 attached to the lower surface 217 of the second connecting portion 216 will slide within the groove 251. The pin 255 operates to keep the two members 205 and 212 connected as the connector 200 is manipulated to seat on the spinal rods. The pin 255 is engageable or connected to the second connecting portion 216 of the second engaging member 212 in any suitable manner. In a preferred embodiment, the pin 255 is connected to the second connecting portion 216 by insertion of the pin 255 into a pin hole 258 defined in the lower surface 217 second connecting portion 216 as depicted in FIGS. 25 and 26. Most preferably, the pin 255 is press fit through the groove 251 and into the pin hole during the manufacture of the connector 200 shown in FIG. 28. However, the provisional means could be assembled by the surgeon or a technician just prior or during the surgery. In one specific embodiment, the total expanded length EL (FIG. 23A) of the connector is 2.7" (68 mm) and the closed length CL (FIG. 23B) is 2.2" (56 mm). In that same embodiment, the distance between the longitudinal members in the expanded configuration is 2.15" (55 mm) and 1.75" (44.5 mm) in the closed configuration.

The connectors and systems of this invention are preferably formed of medical grade stainless steel or similar high strength material. Other biocompatible materials are contemplated provided the material is strong enough to endure the high loads transmitted through the components. Specifically, the systems could be manufactured in 6A14V titanium or 316LVM stainless steel. The connectors can be provided in several different sizes as necessary to accommodate the spinal anatomy at the cervical, thoracic and lumbar segments of the spine.

While the invention has been illustrated and described in detail in the drawings and foregoing description, the same is to be considered as illustrative and not restrictive in character. The connectors of this invention will have configurations of any suitable size or shape designed for the particular application. For example, the second connecting portion 166, 216 of the connectors 150, 200 shown in FIGS. 19–30 will be shaped and sized to be accommodated by the slot 153, 203 of the bridge member 152, 202. The second connecting portion may have a cross-section which is rectangular as shown in FIG. 19, circular or circular interrupted by a flat surface as shown in FIG. 25. Therefore, it is understood that only the preferred embodiments have been shown and described and that all changes and modifications that come within the spirit of the invention are desired to be protected.

What is claimed:

1. A device for linking adjacent longitudinal members engaged to a spine, comprising:

a first engaging member, said first engaging member defining a first fixation portion at a first end and a first connecting portion at a second end;

a second engaging member, said second engaging member defining a second fixation portion at a first end and a second connecting portion at a second end;

a bridge member, said bridge member engagable to each of said engaging members at said first and second connecting portions, wherein:

said bridge member defines a slot, a fastener, and a fastener bore for receiving said fastener, said bore having an axis intersecting said slot;

said second connecting portion being insertable in said slot to intersect said axis of said bore and be clamped therein when said fastener is received in said bore;

each of said fixation portions including:

a fixation surface configured for engaging one of said longitudinal members thereon;

a thru-hole for receiving a wedge member operable to adjustably bear against a corresponding one of said longitudinal members and releasably clamp said corresponding one of said longitudinal members against said fixation surface; and wherein one of said bridge member and said second connecting portion defines a groove and another of said bridge member and said second connecting portion includes a pin engaging said groove to provisionally couple said first and second engaging members.

2. The device of claim 1 wherein:

said bridge member defines said groove on a lower surface, said groove intersecting said slot; and said pin extends from a lower surface of said second connecting portion.

3. The device of claim 2 wherein said lower surface of said second connecting portion defines a pin hole and said pin is inserted through said groove and into said pin hole.

4. The device of claim 3 wherein said pin is press-fit into said pin hole.

5. The device of claim 1 wherein said fastener has a circular head and a hex recess for receiving a driving tool.

6. The device of claim 1 wherein said second connecting portion includes a flat upper surface.

7. The device of claim 6 wherein said fastener includes a flat bearing surface for bearing against said flat upper surface of said second connecting portion when said second connecting portion is inserted into said slot.

8. The device of claim 1 wherein said bridge member defines a longitudinal axis and said thru-holes are oriented at an oblique angle relative to said longitudinal axis.

9. A spinal fixation system comprising:

a pair of longitudinal members;

a first engaging member having a first fixation surface, a first set screw, and a first thru-hole to receive said first set screw, said first set screw being operable to advance through said first thru-hole to bear against a first one of said longitudinal members and clamp said first one of said longitudinal members to said first fixation surface;

a second engaging member having a second fixation surface, a second set screw, and a second thru-hole to receive said second set screw, said second set screw being operable to advance through said second thru-hole to bear against a second one of said longitudinal members and clamp said second one of said longitudinal members to said second fixation surface;

means for linking said first engaging member to said second engaging member, means for provisionally connecting said first and second engaging members together, said connecting means maintaining said first and second engaging members in sliding engagement.

10. The device of claim 9 wherein said linking means includes:

a bridge member integrally attached to said first engaging member and defining a slot and a fastener bore having an axis intersecting said slot for receiving a fastener; and a connecting portion integrally attached to said second engaging member and being insertable in said slot to intersect said axis of said fastener bore, whereby said fastener received in said bore will clamp said connecting portion.

11. The device of claim 10 wherein said connecting means comprises a groove defined by a lower surface of said bridge member, said groove being in communication with said slot; and, a pin attached to a lower surface of said connecting portion, said pin being slidable along said groove.

12. The device of claim 11 wherein said lower surface of said connecting portion defines a pin hole and said pin is inserted through said groove and into said pin hole.

13. The device of claim 12 wherein said pin is press-fit into said pin hole.

14. A spinal fixation system comprising:

a pair of longitudinal members;

a transverse connector to link said longitudinal members, said connector having a first end opposite a second end along a longitudinal axis of said connector, said connector including:

a first member terminating at said first end, said first member including a first fixation surface and a first adjustable wedge member, said first wedge member being configured to adjustably clamp a first one of said longitudinal members against said first fixation surface, said first member defining a slot intersected by a fastener opening;

a second member terminating at said second end, said second member including a second fixation surface, a second adjustable wedge member, and a connecting portion, said second wedge member being configured to adjustably clamp a second one of said longitudinal members against said second fixation surface;

a fastener to clamp said first and second members together; and wherein one of said first and second members defines a groove and another of said first and second members includes a pin engaging said groove, said connecting portion being slidable within said slot to adjust length of said connector over a predetermined range along said longitudinal axis while being provisionally coupled by said pin engaged in said groove, said fastener being operable to advance through said opening to clamp said connection portion to said first member to fix said connector at a desired length selected from said range.

15. The system of claim 14 wherein said first member defines said groove intersecting said slot and said second member defines a pin hole, said pin being inserted through said groove and into said pin hole.

16. The system of claim 15 wherein said pin is press-fit into said pin hole.

17. The system of claim 14 wherein said first member defines a first thru-hole and said second member defines a second thru hole, said first and second thru-holes being oriented at an oblique angle relative to said longitudinal axis.

18. The system of claim 15 wherein said first and second wedge members are each a set screw with a tip contoured to engage a respective one of said longitudinal members.

19. The system of claim 18 wherein said fastener is a screw having a tip with a generally flat bearing surface for engaging a generally flat upper surface of said connecting portion.

20. The system of claim 15 wherein said first member includes a first receptacle for receiving said first one of said longitudinal members, and said second member includes a second receptacle for receiving said second one of said longitudinal members, said slot and said connecting portion being positioned along said longitudinal axis between said first and second receptacles.

* * * * *